United States Patent [19]

Fünfschilling

[11] 4,316,042
[45] Feb. 16, 1982

[54] SUBSTITUTED CARBOXYALKOXYAMINODIHYDROBEN- ZOPHENONES

[75] Inventor: Peter Fünfschilling, Basel, Switzerland

[73] Assignee: Sandoz Ltd., Basel, Switzerland

[21] Appl. No.: 67,070

[22] Filed: Aug. 15, 1979

[30] Foreign Application Priority Data

Aug. 16, 1978 [CH]  Switzerland ................. 8793/78

[51] Int. Cl.³ ........................... C07C 125/065
[52] U.S. Cl. ........................... 560/27; 560/9; 560/21; 560/29; 560/30; 560/115; 560/156; 544/315; 544/318; 568/335; 568/337
[58] Field of Search ......................... 560/27, 21

[56] References Cited

U.S. PATENT DOCUMENTS

| | | | |
|---|---|---|---|
| 3,641,147 | 2/1972 | Topliss | 560/27 |
| 3,846,477 | 11/1974 | Welstead, Jr. | 560/27 |
| 3,937,705 | 2/1976 | Hardtmann | |
| 4,021,469 | 5/1974 | Weston | 560/27 |
| 4,067,868 | 1/1978 | Ishizumi | 560/21 |
| 4,220,747 | 9/1980 | Preziosi et al. | 560/157 |

OTHER PUBLICATIONS

Holmes, Organic Reactions, John Wiley & Sons, Inc., NY. vol. IV, pp. 60–63, 78–90, 152–169, 1962.
Dauben et al., Organic Reactions, John Wiley & Sons, NY. vol. 24, p. 288–289, 1976.
Migrdichian, Organic Synthesis, Reinhold Publishing Corp, NY, vol. 2, 1205–1208, 1960.

Primary Examiner—G. T. Breitenstein
Attorney, Agent, or Firm—Gerald D. Sharkin; Richard E. Vila

[57] ABSTRACT

Compounds of the formula II:

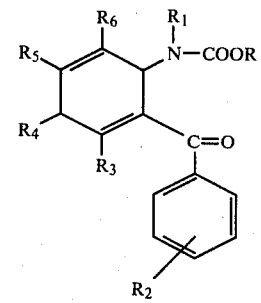

are produced by reacting a compound of the formula III

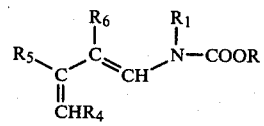

with a compound of the formula IV:

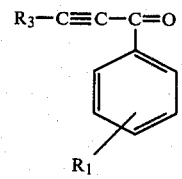

wherein
$R_1$ is hydrogen, alkyl of 1 to 5 carbon atoms, cycloalkyl of 3 to 6 carbon atoms, alkyl of 1 to 4 carbon atoms substituted by cycloalkyl of 3 to 6 carbon atoms, polyhaloalkyl of 1 to 5 carbon atoms, allyl, propargyl, enzyl or aryl,
$R_2$ is hydrogen, halogen, alkyl or alkoxy, each of 1 to 4 carbon atoms, trifluoromethyl, nitro, alkylamino or dialkylamino, wherein the alkyl groups have 1 to 4 carbon atoms, or aryl,
$R_3$ is hydrogen, halogen, alkyl or alkoxy, each of 1 to 4 carbon atoms, or aryl,
$R_4$ is hydrogen, nitro, halogen, alkyl or alkoxy each of 1 to 4 carbon atoms or aryl,
$R_5$ is hydrogen, halogen, alkyl, alkylthio or alkoxy each of 1 to 4 carbon atoms, nitro, trifluoromethyl or aryl,
$R_6$ is hydrogen, halogen, alkyl of 1 to 4 carbon atoms, benzyl or aryl, and
$R$ is alkyl of 1 to 4 carbon atoms. Compounds II can be dehydrogenated and used as intermediates for 4-phenyl-quinazolin-2(1H)-ones.

6 Claims, No Drawings

SUBSTITUTED CARBOXYALKOXYAMINODIHYDROBENZOPHENONES

The present invention relates to a process for the production of 2-aminobenzophenone derivatives.

More particularly, this invention provides a process for the production of compounds of formula I,

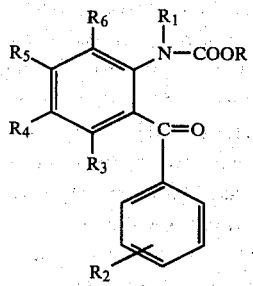

wherein
- $R_1$ is hydrogen, alkyl of 1 to 5 carbon atoms, cycloalkyl of 3 to 6 carbon atoms, alkyl of 1 to 4 carbon atoms substituted by cycloalkyl of 3 to 6 carbon atoms, polyhaloalkyl of 1 to 5 carbon atoms, allyl, propargyl, benzyl or aryl,
- $R_2$ is hydrogen, halogen, alkyl or alkoxy, each of 1 to 4 carbon atoms, trifluoromethyl, nitro, alkylamino or dialkylamino, wherein the alkyl groups have 1 to 4 carbon atoms, or aryl,
- $R_3$ is hydrogen, halogen, alkyl or alkoxy, each of 1 to 4 carbon atoms, or aryl,
- $R_4$ is hydrogen, nitro, halogen, alkyl or alkoxy each of 1 to 4 carbon atoms or aryl,
- $R_5$ is hyrdogen, halogen, alkyl, alkylthio or alkoxy each of 1 to 4 carbon atoms, nitro, trifluoromethyl or aryl,
- $R_6$ is hydrogen, halogen, alkyl of 1 to 4 carbon atoms, benzyl or aryl, and
- R is alkyl of 1 to 4 carbon atoms.

Conveniently aryl is phenyl.

In accordance with the invention, the compounds of formula I are obtained by oxidising compounds of formula II,

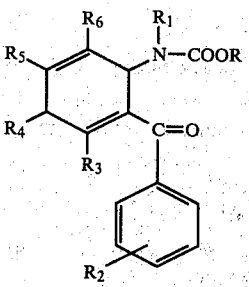

wherein $R_1$–$R_6$ and R are as defined above.

The process is conveniently effected in an inert organic solvent, such as ethanol, benzene, dioxane or chloroform. The reaction temperature is conveniently from room temperature to reflux temperature. The oxidation may be effected with e.g. manganese dioxide, selenium dioxide, 2,3-dichloro-5,6-dicyano-1,4-benzochinone, palladium on active charcoal or atmospheric oxygen.

The compounds of formula II may be produced by reacting a compound of formula III,

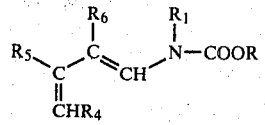

wherein $R_1$, $R_4$–$R_6$ and R are as defined above, with a compound of formula IV,

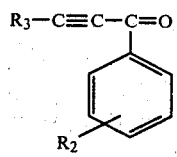

wherein $R_2$ and $R_3$ are as defined above.

The reaction is conveniently effected in the presence or absence of an inert organic solvent. Suitable solvents include hexane, toluene or chloroform. The reaction temperature is conveniently from 20° to 120° C.

The compounds of formula III may be produced by reacting a compound of formula V,

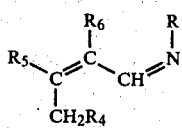

wherein $R_1$ and $R_4$–$R_6$ are as defined above, with a compound of formula VI,

X—COOR  VI wherein R is as defined above and X is chlorine or bromine.

The reaction is suitably effected at room temperature in an inert organic solvent, such as benzene, toluene, hexane or methylene dichloride. An acid binding agent, e.g. diethylaniline or 2,4,6-trimethylpyridine may be used.

The compounds of formulae IV, V and VI are either known or may be produced in conventional manner.

The compounds of formula I are useful intermediates. According to the process described in for example German Patent 2 230 393 and DOS 2 230 394 they can be reacted with organic acid ammonium salt to give 4-phenyl-2(1H)-quinazolinones of formula A

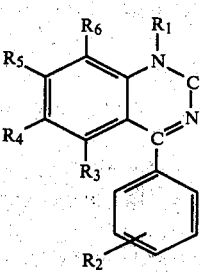

wherein $R_1$–$R_6$ are as defined above, which have pharmaceutical properties.

Furthermore, the compounds of formula I can be hydrolysed and reacted with halogeno acetic acid halogenides to give compounds of formula B,

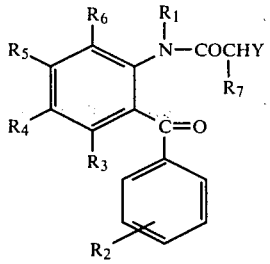

wherein $R_1$–$R_6$ are as defined above, $R_7$ is hydrogen, alkyl or aryl and Y is halogen. Compounds of formula B can be cyclised to give pharmaceutically active 2,3-dihydro-1H-1,4-benzodiazepin-2-ones in known manner.

In the compounds of formula I, where $R_1$ is alkyl, it is preferably isopropyl. When it is polyhaloalkyl, it is preferably 2,2,2-trifluoroethyl and when it is cycloalkylalkyl, it is suitably cyclopropylmethyl. $R_2$ is suitably hydrogen and halo, particularly fluoro, more particularly 4-fluoro.

A particularly preferred group of compounds I are those of formula Ia,

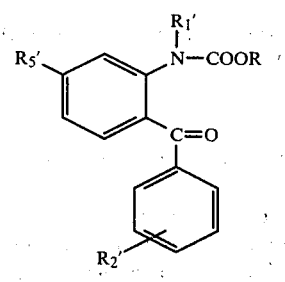

wherein
  $R_1'$ is alkyl of 1 to 5 carbon atoms other than tertiary alkyl, in which the tert. carbon atom is directly bound to the nitrogen atom; allyl or propargyl;
  $R_2'$ is hydrogen, fluorine, chlorine, bromine, alkyl or alkoxy each of 1 to 3 carbon atoms or trifluormethyl,
  $R_5'$ is hydrogen, fluorine, chlorine, bromine, alkyl, alkylthio or alkoxy each of 1 to 3 carbon atoms, trifluoromethyl or nitro and
  R is alkyl of 1 to 4 carbon atoms,
which can be cyclised in known manner as described above to quinazolinones.

$R_1'$ is preferably alkyl, particularly isopropyl,
$R_2'$ is preferably hydrogen or fluorine, especially 4-fluorine,
$R_5'$ is preferably alkyl, particularly methyl.
The following Examples illustrate the invention.

EXAMPLE 1

2-(N-Isopropyl-N-carbomethoxyamino)-4-methyl-4'-fluorobenzophenone (a) N-Isopropyl-N-(3-methyl-1,3-butadienyl)-carbamic acid methyl ester To a stirred solution of 657 g diethylaniline in 2 liter toluene is added dropwise over ca. 5 minutes 416 g methyl chloroformate. Then to the stirred mixture 500 g N-(3-methyl-2-butenyliden)-isopropylamine in 500 ml toluene is added dropwise over 2 hours, maintaining the temperature between 25° and 30° C. Stirring is continued for 1 hour upon completion of the addition and the reaction mixture is treated with 400 ml of water and 90 ml conc. hydrochloric acid. The organic phase is washed with 600 ml of saturated aqueous sodium bicarbonate solution and with 600 ml water, dried and evaporated in vacuo to give the heading compound.

(b)
2-(N-Isopropyl-N-carbomethoxyamino)-4-methyl-4'-fluoro-2,5-dihydrobenzophenone To a stirred suspension of 67,9 g 4-fluorobenzoylacetylene in 160 ml hexane under reflux is added dropwise within 1 hour 78,8 g N-isopropyl-N-(3-methyl-1,3-butadienyl)-carbamic acid methylester in 40 ml hexane. After the addition is completed, the reaction mixture is stirred for additional 6 hours under reflux, and then cooled to room temperature, whereby the heading compound precipitates, m.p. 98°–102° C.

(c)
2-(N-Isopropyl-N-carbomethoxyamino)-4-methyl-4'-fluorobenzophenone 20 g 2-(N-isopropyl-N-carbomethoxyamino)-4-methyl-4'-fluoro-2,5-dihydrobenzophenone and 100 g manganese dioxide in 200 ml chloroform are stirred 4 hours under reflux. The reaction mixture is cooled, filtered and evaporated in vacuo. The residue is recrystallised from hexane to obtain the heading compound, m.p. 92°–94° C.

EXAMPLE 2

In manner analogous to that described in Example 1 and by employing appropriate starting materials in approximately equivalent amounts, the following compounds of formula I may be obtained:
  (a) 2-(N-isopropyl-N-carboethoxyamino)-4-methyl-benzophenone, m.p. 91°–92° C.,
  (b) 2-(N-isopropyl-N-carbomethoxyamino)-4-methyl-benzophenone, m.p. 65°–66° C.,
via the corresponding compounds of formula II:
  (a') 2-(N-isopropyl-N-carboethoxyamino)-4-methyl-2,5-dihydrobenzophenone,
  (b') 2-(N-isopropyl-N-carbomethoxyamino)-4-methyl-2,5-dihydrobenzophenone, m.p. 72°–75° C.

What we claim is:

1. A compound of the formula:

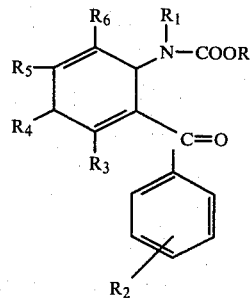

wherein
R₁ is hydrogen, alkyl of 1 to 5 carbon atoms, cycloalkyl of 3 to 6 carbon atoms, alkyl of 1 to 4 carbon atoms substituted by cycloalkyl of 3 to 6 carbon atoms, polyhaloalkyl of 1 to 5 carbon atoms, allyl, propargyl, benzyl or phenyl, R₂ is hydrogen, halogen, alkyl or alkoxy, each of 1 to 4 carbon atoms, trifluoromethyl, nitro, alkylamino or dialkylamine, wherein the alkyl groups have 1 to 4 carbon atoms, or phenyl, R₃ is hydrogen, halogen, alkyl or alkoxy, each of 1 to 4 carbon atoms, or phenyl, R₄ is hydrogen, nitro, halogen, alkyl or alkoxy each of 1 to 4 carbon atoms or phenyl, R₅ is hydrogen, halogen, alkyl, alkylthio or alkoxy each of 1 to 4 carbon atoms, nitro, trifluoromethyl or phenyl, R₆ is hydrogen, halogen, alkyl of 1 to 4 carbon atoms, benzyl or phenyl, and R is alkyl of 1 to 4 carbon atoms.

2. A compound of claim 1 in which R₁ is alkyl of 1 to 5 carbon atoms other than tertiary alkyl in which the tertiary carbon atom is directly bound to the nitrogen atom, allyl or propargyl, R₂ is hydrogen, fluoro, chloro, bromo, alkyl of 1 to 3 carbon atoms, alkoxy of 1 to 3 carbon atoms or trifluoromethyl, R₅ is hydrogen, fluoro, chloro, bromo, alkyl of 1 to 3 carbon atoms, alkoxy of 1 to 3 carbon atoms, alkylthio of 1 to 3 carbon atoms or trifluoromethyl and R₃, R₄ and R₆ each hydrogen.

3. A compound of claim 2 in which R₁ is isopropyl, R₂ is hydrogen or 4-fluoro and R₅ is methyl.

4. The compound of claim 3 in which R₂ is hydrogen and R is methyl.

5. The compound of claim 3 in which R₂ is 4-fluoro and R is methyl.

6. The compound of claim 3 in which R₂ is hydrogen and R is ethyl.

* * * * *